(12) United States Patent
Löfqvist et al.

(10) Patent No.: US 7,189,323 B2
(45) Date of Patent: Mar. 13, 2007

(54) METHOD FOR BIOLOGICAL PURIFICATION OF WATER USING A CARRIER MATERIAL

(75) Inventors: Anders Löfqvist, Vallåkra (SE); Thomas Welander, Furulund (SE)

(73) Assignee: AnoxKaldnes AS, Lund (SE)

( * ) Notice: Subject to any disclaimer, the term of this patent is extended or adjusted under 35 U.S.C. 154(b) by 179 days.

(21) Appl. No.: 10/895,920

(22) Filed: Jul. 22, 2004

(65) Prior Publication Data
US 2005/0072732 A1    Apr. 7, 2005

(51) Int. Cl.
*C02F 3/00* (2006.01)
(52) U.S. Cl. .............. 210/615; 210/616; 210/150; 261/DIG. 72
(58) Field of Classification Search .......... 210/150, 210/151, 616, 617, 615, 620; 261/DIG. 72
See application file for complete search history.

(56) References Cited

U.S. PATENT DOCUMENTS

| 2,071,591 | A | * | 2/1937 | Tholin | 210/616 |
| 2,375,336 | A | * | 5/1945 | Weitkamp | 261/DIG. 72 |
| 4,122,011 | A | * | 10/1978 | Strigle, Jr. | 210/150 |
| 4,382,046 | A | * | 5/1983 | Frohwerk | 261/DIG. 72 |
| 4,385,988 | A | * | 5/1983 | Hypponen | 210/150 |
| 4,477,394 | A | * | 10/1984 | Armstrong et al. | 210/150 |
| 4,566,971 | A | * | 1/1986 | Reimann et al. | 210/616 |
| 4,705,634 | A | * | 11/1987 | Reimann et al. | 210/616 |
| 5,401,398 | A | * | 3/1995 | McManus | 210/150 |
| 5,707,416 | A | * | 1/1998 | Sudrabin | 210/151 |
| 5,783,069 | A | * | 7/1998 | Frank | 210/150 |

FOREIGN PATENT DOCUMENTS

| WO | WO 91/11396 | 8/1991 |
| WO | WO 95/25072 | 9/1995 |
| WO | WO 98/39254 | 9/1998 |

* cited by examiner

*Primary Examiner*—Christopher Upton

(57) ABSTRACT

A method for biological purification of water such as wastewater using a carrier material is disclosed, wherein the water is treated in a reactor containing carriers for biofilm growth. These carriers are kept in movement in the water and are designed so that they have well-defined passages or compartments providing a surface for biofilm growth, which is protected against collision with the surfaces of other carriers. The carriers have a width or diameter greater than 20 mm, the protected area is larger than 1000 $m^2/m^3$ carrier element volume, the length of the passages or the depth of the compartments in the carrier elements as a mean value is smaller than 6 mm or smaller than 3 mm, respectively, and the ratio between the passage lengths or compartment depths and the longest dimension of the inlet openings to the passages or compartments, respectively, is smaller than 3.

20 Claims, 3 Drawing Sheets

METHOD FOR BIOLOGICAL PURIFICATION OF WATER USING A CARRIER MATERIAL

Figure 1:
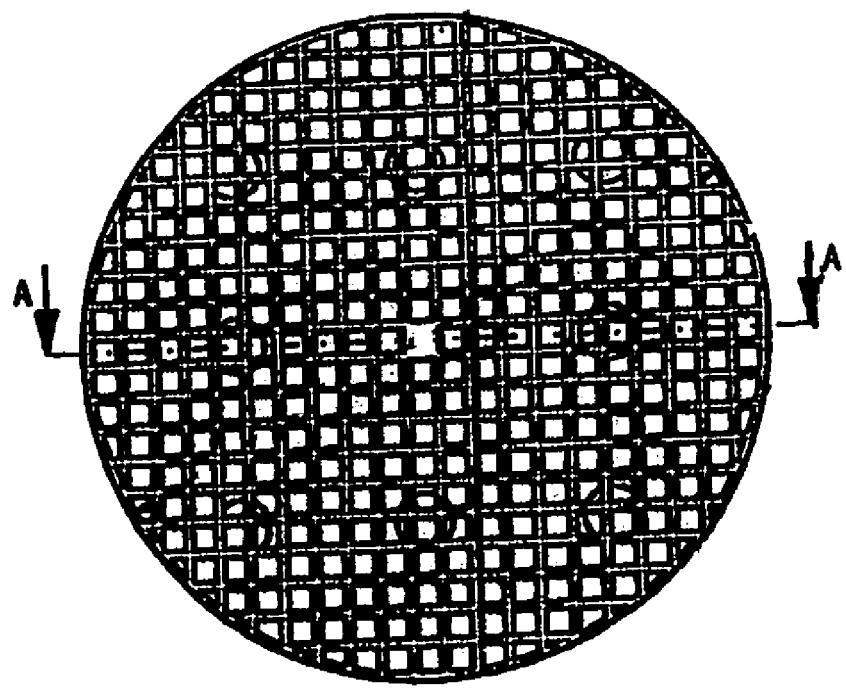

The invention relates to a method for biological purification of water such as wastewater wherein a carrier material is used.

In biological purification of water or wastewater the water is passed through some type of reactor (a vessel or another space) wherein micro-organisms are utilized for converting impurities existing in the water to harmless end products such as carbon dioxide and water. The purification can be performed under supply of air (aerobically) or without supply of air (anaerobically). In order to increase the efficiency of the purification process it is common to aim at a high content of active micro-organisms in the process by preventing such organisms to escape together with the purified water, either by allowing the micro-organisms to grow suspended in the reactor and separating them from the water in a separation step after the reactor and returning the micro-organisms to the reactor (e.g. the activated sludge process), or by introducing some type of carrier material into the process on the surfaces of which the micro-organisms can grow as a biofilm and thus are retained in the process (the biofilm process). There are also mixtures of these two process types, referred to as hybrid processes, wherein the carrier material is introduced into the activated sludge process so that suspended micro-organisms as well as biofilm growing micro-organisms can be utilized in the process.

The biofilm process has several advantages as compared with the activated sludge process. I.a. higher loads can be utilized and the biofilm processes are substantially less sensitive to variations and disturbances. Most conventional biofilm processes are based on packing of carrier material in the purification reactor said material comprising fill bodies or blocks which are maintained fixed and immovable in the process. These embodiments of the process involve the risk of clogging of the biofilm bed by biomass or another particulate material and formation of dead zones in the process, wherein the contact between the water and the active micro-organisms is unsatisfactory.

In another type of biofilm process which has been very successful during recent years there is utilized a carrier material which is kept in suspension and in movement in the process, referred to as the MBBR process, "Moving Bed Biofilm Reactor". The carrier material with micro-organisms growing thereon is maintained in the process by passing outgoing water through a strainer (sieve or grid) having an aperture diameter or slot width which is so small that the carrier material cannot pass therethrough. The advantage of this type of process is i.a. that the risk of clogging of the bed and formation of dead zones is eliminated.

The use of a carrier material which is kept in suspension and movement in the process was originally reported for different hybrid process applications, i.e. suspended carriers were supplied to activated sludge processes in order to improve the function thereof. Carriers which have been used for this purpose include pieces of foamed rubber (EP 0 142 123), different types of cylindrical fill bodies (Bundesministerium für Forschung und Technologie, "Einsatz von Schwebekörper zur Erhöhung der" by Dr. D. Dengler, H. Lang, A. Baum, Forschungsbericht 02 WA 8538, January 1988, pages 12 and 13), carriers including semispherical bodies having inner walls (DE 30 17 439), "hedgehog-like" carriers, perforated spheres, and crossed plates (EP 0 058 974).

The first genuine biofilm process with suspended carrier material (MBBR) was presented at the beginning of the nineties (EP 0 575 314 B1) and was rapidly very successful. The process is based on the use of a carrier material with a surface which is at least 1.5 times larger than the surface of smooth elements having the same dimensions, and a density ranging from 0.90 to 1.20, the surface being partly protected against wearing against other carrier elements, and with walls allowing ample passage of water through the carriers. The preferred embodiment of these carriers comprising pieces of a hose having inside partitions and outside fins. Such carriers having a diameter ranging from 8 to 15 mm have been utilized successfully in more than 150 full-scale installations of the MBBR process.

Similar carriers for the MBBR process are disclosed in Patent Abstracts of Japan, Vol. 14, No. 509, wherein the carriers are described as hoselike elements with an outside diameter ranging from 2 to 20 mm, a density ranging from 1.0 to 1.02, a ratio between length and diameter ranging from 0.3 to 3.0, and several longitudinal openings through the carrier each having a diameter of at least 1 mm.

Carriers comprising pieces of extruded hose of this type which have been developed for the MBBR process then have been used also in hybrid processes (marketing material from EVU Entwicklung von Umwelttechnik GmbH; marketing material from Conor Pacific Environmental Technologies Inc.).

Since the carriers in the MBBR process are exposed to repeated collisions with each other the surfaces which are exposed to other carriers are kept clean from biofilm growth. The efficiency of the process therefore is highly dependent of the area which is protected against collisions for example in inner passages or compartments (bottom holes) in the carriers. The aim at a large protected area initially led to only small carriers, smaller than 15 mm, being used in the MBBR process. Those skilled in the art considered it impossible to provide a sufficiently large protected area for large carriers, larger than about 15 mm, without the transport of water, impurities and oxygen to the biofilm being heavily impaired. In a further development the critical parameters were identified which are required in order to guarantee a satisfactory mass transport also in larger carriers having a relatively large protected area (EP 0 750 591). In many applications, particularly when the wastewater contains many particles, it is an advantage to utilize large carriers because grids or strainers having large apertures can be used for maintaining these carriers in the process. In one embodiment available on the market this carrier is defined as a cylindrical carrier element built up by radial walls which are interconnected to a structure similar to a turbine wheel, which is open in the centre. Carriers of this type in sizes ranging from 30 to 60 mm and having a protected area up to about 300 $m^2/m^3$ carrier bulk volume have been successfully used in about 50 MBBR installations. With these prior art embodiments it has not been possible, however, to use in practice large carriers, >15 mm with an effective protected area >400 $m^2/m^3$ carrier bulk volume without problems being involved in mass transport to the biofilm. This is also explained in EP 0 750 591. "If the carrier elements are designed so as to have a very large surface, >500 $m^2/m^3$, it can however be difficult to avoid that the passages through the carrier element will be so narrow that they are stopped by the growth". >500 $m^2/m^3$ refers to a carrier element volume≈400 $m^2/m^3$ bulk volume.

For small carriers, <15 mm, according to prior art embodiments a practical limit for the effective protected area that can be obtained without mass transport limitations, has been about 500 $m^2/m^3$ carrier bulk volume.

The primary object of the present invention is to considerably increase the capacity of MBBR and hybrid processes, and the invention relates to a method for biological purification of water wherein the water is supplied to a reactor containing carriers for biofilm growth, which are kept in movement in the water in the reactor and are dimensioned to be retained in the reactor by a strainer allowing discharge of the water from the reactor through the strainer openings, and which have well defined passages or compartments providing a surface for the biofilm growth, which is protected against collision with surfaces of other carrier elements.

Said object is achieved by the method of the invention having the characterizing features according to claim 1 the carrier material as a consequence thereof combines a large size in two dimensions with an effective protected area which is considerably larger than that of prior art embodiments, without problem being involved in the mass transport to the biofilm.

Use of the carriers according to the invention provides great advantages as compared with the use of carriers according to prior art embodiments due to the fact that considerably larger effective protected surfaces can be provided in the process, which increases the capacity of the process and provides the possibility to substantially reduce the volume of the purification reactor.

Considering the prior art discussed above it was not obvious to the skilled man to design the carriers used in the method of the invention as defined in claim 1 in order to achieve a substantial increase of the efficiency of the MBBR processes or hybrid processes.

Advantageous features of the invention are defined in the dependent claims.

Figure 2:
Figure 3:
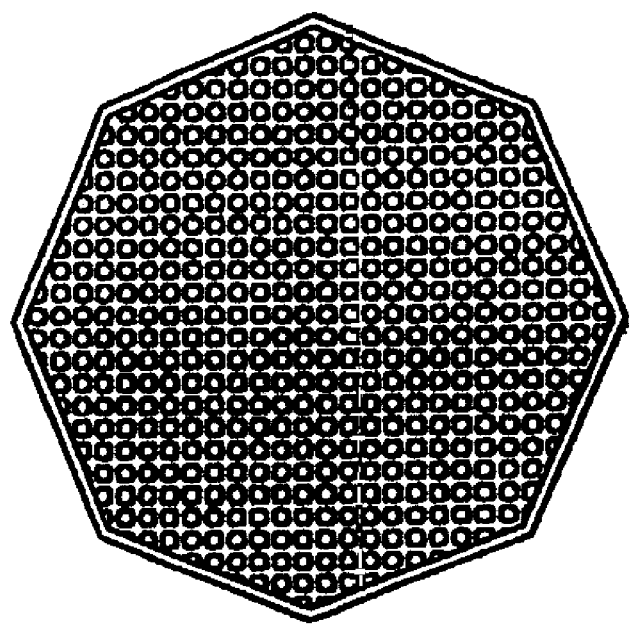
Figure 4:
Figure 5:
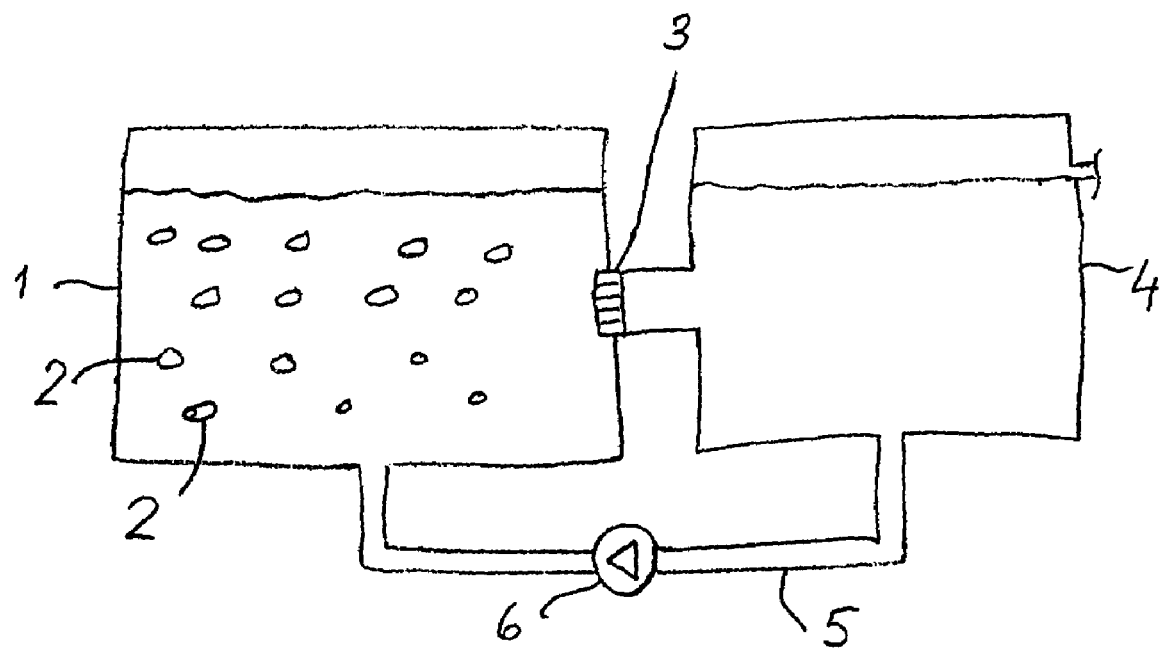

In order to explain the invention in more detail two embodiments will be described below reference being made to the accompanying drawings in which FIGS. 1 and 2 are a side view and a cross sectional view, respectively of a first embodiment of the carrier element according to the invention the cross sectional view being taken along line A—A in FIG. 1, and FIGS. 3 and 4 are views similar to FIGS. 1 and 2 and disclose a second embodiment according to the invention. FIG. 5 is a schematic view of a reactor plant.

The carrier element according to the first embodiment can be described as a circular plate having a plurality of passages formed by through square apertures through the plate with walls which provide a surface protected against wear against other carrier elements. The diameter of the carrier element is 30 mm. The thickness of the plate in the passage direction is 2 mm and the apertures have a side length of 1 mm which provides a protected area of about 1950 $m^2/m^3$ carrier element volume, and a ratio between the length of the passages and the greatest dimension of the apertures (the diagonal) of 1.4. Generally, the diameter of the carrier element or the width thereof should be greater than 20 mm, the length of the passages should be smaller than 6 mm, and the ratio between the length of the passages and the longest dimension of the inlet apertures should be less than 3, preferably less than 2.5, particularly less than 2. The protected area should generally be at least 1000 $m^2/m^3$ carrier element volume, preferably at least 1250 $m^2/m^3$ carrier element volume, particularly at least 1500 $m^2/m^3$ carrier element volume.

The carrier according to the second embodiment can be described as an octagon plate having a plurality of circular bottom holes into the plate from both sides, which form compartments and provide a surface protected against wear against other carriers. The diameter of the carrier over the corners is 52 mm. The thickness of the plate is 4.5 mm. The depth of the compartments is 2 mm, and the diameter of the inlet openings of the compartments is 1.5 mm, which provides a protected area of 1330 $m^2/m^3$ carrier element volume and a ratio between the depth of the compartments and the longest dimension (the diameter) of the openings of 1.33.

In the method of the invention the water such as wastewater is supplied to a space such as a vessel referred to as a reactor, containing carriers of the invention, e.g. of one or the other of the embodiments described above. The carriers are kept in movement in the water in the reactor from which the water is discharged through the openings of a strainer. The carriers should be dimensioned in relation to the strainer openings under consideration of the parameters of the invention such that they do not pass through the strainer openings but are retained in the reactor.

The combination of a size, area, passage length and compartment depth, respectively, and the inlet opening dimension in relation to the passage length or the compartment depth, respectively, as set out above provides a carrier having substantially improved properties in MBBR or hybrid processes than carriers used before. A very important feature of the invention is that the passage length or compartment depth, respectively, is adapted to the dimension of the inlet openings according to the ratio mentioned above.

At extensive comparisons between the invention and preferred embodiments of prior art carriers the invention was found to provide a considerably higher capacity of MBBR or hybrid processes. At comparison relating to nitrification of municipal wastewater in three parallel MBBR processes each filled with carrier material up to 50% of the volume of the process reactor the capacities according to Table 1 below were recorded.

Thus, the process capacity could be increased at least 3 times by using carrier material according to the invention.

TABLE 1

Comparison between the invention and the use of prior art carrier material.

| Carrier type | Nitrification rate, g $NH4-N/m^3$ reactor, h |
|---|---|
| K1 (EP 0 575 314 B1) | 11.5 |
| Natrix 10/10 (EP 0 750 591) | 8.3 |
| The invention, the embodiment according to FIG. 1 | 34.1 |

FIG. 5 shows a reactor 1 with water. In the water, several carrier elements 2 are arranged. A strainer 3 having strainer openings retaining the carrier elements in the reactor, is arranged in the reactor 1 for passing water to a separator tank 4, in which sludge may settle. A return conduit 5 passes the separated sludge back to the reactor by means of a pump 6.

The invention claimed is:

1. Method for biological purification of water, comprising the step of:

supplying water to a reactor containing carrier elements for biofilm growth, which are kept in movement in the water in the reactor and are dimensioned to be retained in the reactor by a strainer allowing discharge of the water from the reactor through strainer openings, said carrier elements having passages providing a protected area for the biofilm growth which is protected against collision with other carrier elements, wherein each carrier element has a width or diameter greater than 20 mm, the protected area is larger than 1000 m$^2$/m$^3$ carrier element volume, the passage length in the carrier element as a mean value is smaller than 6 mm and the ratio between the passage length and the longest dimension of the inlet openings of the passages is smaller than 3, wherein each carrier element is a plate having a large diameter to depth ratio and having a plurality of through apertures forming said passages.

2. The method according to claim 1, wherein suspended biomass in discharged water is separated from the water and returned to the reactor so that the reactor will contain biomass suspended in the water therein, as well as biomass growing on the carriers.

3. The method according to claim 1, wherein said protected area is larger than 1250 m$^2$/m$^3$ carrier element volume.

4. The method according to claim 1, wherein said protected area is larger than 1500 m$^2$/m$^3$ carrier element volume.

5. The method according to claim 1, wherein the passage length in the carrier element as a mean value is smaller than 4.5 mm.

6. The method according to claim 1, wherein the passage length in the carrier element as a mean value is smaller than 3 mm.

7. The method according to claim 1, wherein the ratio between the passage length and the longest dimension of the inlet openings of the passages is smaller than 2.5.

8. The method according to claim 1, wherein the ratio between the passage length and the longest dimension of the inlet openings of the passages is smaller than 2.

9. Method for biological purification of water, comprising the step of:
supplying water to a reactor containing carrier elements for biofilm growth, which are kept in movement in the water in the reactor and are dimensioned to be retained in the reactor by a strainer allowing discharge of the water from the reactor through strainer openings, said carrier elements having compartments providing a protected area for the biofilm growth which is protected against collision with other carrier elements, wherein each carrier element has a width or diameter greater than 20 mm, the protected area is larger than 1000 m$^2$/m$^3$ carrier element volume, the compartment depth in the carrier element as a mean value is smaller than 3 mm and the ratio between the compartment depth and the longest dimension of the inlet openings of the compartment is smaller than 3, wherein each carrier element is a plate having a large diameter to depth ratio and having a plurality of blind holes forming said compartments, which extend into the plate from both sides thereof.

10. The method according to claim 9, wherein suspended biomass in discharged water is separated from the water and returned to the reactor so that the reactor will contain biomass suspended in the water therein, as well as biomass growing on the carriers.

11. The method according to claim 9, wherein said protected area is larger than 1250 m$^2$/m$^3$ carrier element volume.

12. The method according to claim 9, wherein said protected area is larger than 1500 m$^2$/m$^3$ carrier element volume.

13. The method according to claim 9, wherein the compartment depth as a mean value is smaller than 2.5 mm.

14. The method according to claim 9, wherein the compartment depth as a mean value is smaller than 2 mm.

15. The method according to claim 9, wherein the ratio between the compartment depth and the longest dimension of the inlet openings of the compartments is smaller than 2.5.

16. The method according to claim 9, wherein the ratio between the compartment depth and the longest dimension of the inlet openings of the compartments is smaller than 2.

17. A reactor for biological purification of water, comprising:
carrier elements for biofilm growth, which are arranged in water in the reactor;
a strainer for retaining the carrier elements in the reactor and for discharging the water from the reactor through strainer openings;
said carrier elements having passages providing a protected area for the biofilm growth, which is protected against collision with other carrier elements,
wherein each carrier element has a width or diameter greater than 20 mm,
the protected area is larger than 1000 m$^2$/m$^3$ carrier element volume,
the passage length in the carrier elements as a mean value is smaller than 6 mm, and
the ratio between the passage length and the longest dimension of the inlet openings of the passages is smaller than 3,
wherein each carrier element is a plate having a large diameter to depth ratio and having a plurality of through apertures forming said passages.

18. A reactor for biological purification of water, comprising:
carrier elements for biofilm growth, which are arranged in water in the reactor;
a strainer for retaining the carrier elements in the reactor and for discharging the water from the reactor through strainer openings;
said carrier elements having compartments providing a protected area for the biofilm growth, which is protected against collision with other carrier elements,
wherein each carrier element has a width or diameter greater than 20 mm,
the protected area is larger than 1000 m$^2$/m$^3$ carrier element volume,
the compartment depth in the carrier elements as a mean value is smaller than 3mm, and
the ratio between the compartment depth and the longest dimension of the inlet openings of the compartments is smaller than 3,
wherein each carrier element is a plate having a large diameter to depth ratio and having a plurality of blind holes forming said compartments, which extend into the plate from both sides thereof.

19. A carrier element for use in a reactor for biological purification of water, comprising:
passages providing a protected area for biofilm growth, which is protected against collision with other carrier elements,
wherein each carrier element has a width or diameter greater than 20 mm,
the protected area is larger than 1000 m$^2$/m$^3$ carrier element volume,
the passage lenth in each carrier element as a mean value is smaller than 6 mm, and
the ratio between the passage length and the longest dimension of the inlet openings of the passages is smaller than 3, wherein the carrier element is a plate having a large diameter to depth ratio and having a plurality of through apertures forming said passages.

20. A carrier element for use in a reactor for biological purification of water, comprising:

compartments providing a protected area for biofilm growth, which is protected against collision with other carrier elements, wherein each carrier element has a width or diameter greater than 20 mm, the protected area is larger than 1000 $m^2/m^3$ carrier element volume, the compartment depth in each carrier element as a mean value is smaller than 3 mm, and the ratio between the compartment depth and the longest dimension of the inlet openings of the compartments is smaller than 3, wherein the carrier element is a plate having a large diameter to depth ratio and having a plurality of blind holes forming said compartments, which extend into the plate from both sides thereof.

* * * * *